US008403666B2

(12) United States Patent
Tarr

(10) Patent No.: US 8,403,666 B2
(45) Date of Patent: *Mar. 26, 2013

(54) COMBINATION ROTATING DENTAL CLEANING BRUSH AND PASTE DEVICE

(76) Inventor: Daniel Edward Tarr, Tulsa, OK (US)

(*) Notice: Subject to any disclaimer, the term of this patent is extended or adjusted under 35 U.S.C. 154(b) by 0 days.

This patent is subject to a terminal disclaimer.

(21) Appl. No.: 13/275,082

(22) Filed: Oct. 17, 2011

(65) Prior Publication Data

US 2012/0034575 A1    Feb. 9, 2012

Related U.S. Application Data

(63) Continuation-in-part of application No. 10/906,861, filed on Mar. 9, 2005, now Pat. No. 8,038,441, which is a continuation-in-part of application No. 10/418,235, filed on Apr. 17, 2003, now Pat. No. 6,875,017.

(60) Provisional application No. 60/404,563, filed on Aug. 20, 2002.

(51) Int. Cl.
*A61C 3/06* (2006.01)

(52) U.S. Cl. ........................................................ 433/125

(58) Field of Classification Search .................. 433/125, 433/126, 82, 83, 85, 87, 89; 401/148, 152, 401/153, 156, 272; 222/167, 168, 169, 206, 222/215
See application file for complete search history.

(56) References Cited

U.S. PATENT DOCUMENTS

| 3,389,468 | A |   | 6/1968  | Lewis et al. |
| 3,579,835 | A | * | 5/1971  | Levenson ........................ 433/82 |
| 4,014,100 | A |   | 3/1977  | Spotteck |
| 4,266,933 | A |   | 5/1981  | Warden et al. |
| 4,954,082 | A |   | 9/1990  | Weissman |
| 5,062,796 | A |   | 11/1991 | Rosenberg |
| 5,642,994 | A |   | 7/1997  | Chipian et al. |
| 5,692,901 | A |   | 12/1997 | Roth et al. |
| 5,871,353 | A |   | 2/1999  | Pierce et al. |
| 6,083,000 | A |   | 7/2000  | Charlton |
| 6,257,886 | B1 | * | 7/2001 | Warner ......................... 433/125 |
| 6,382,971 | B1 | * | 5/2002 | Randolph ....................... 433/82 |
| 6,875,017 | B1 | * | 4/2005 | Tar .............................. 433/125 |
| 2005/0026103 | A1 |   | 2/2005 | Wasylucha |
| 2005/0032022 | A1 |   | 2/2005 | Jaffe |

* cited by examiner

*Primary Examiner* — Yogesh Patel
(74) *Attorney, Agent, or Firm* — Head, Johnson & Kachigian, P.C.

(57) ABSTRACT

The combination rotating dental cleaning brush and paste device. The device includes a housing having a rotating shaft therethrough. A compressible tube has two opposed ends, a first end which is rotated by the shaft and a second end having an opening therethrough. A brush is integral with, connected to, and rotated by the second end of the tube. Compression of the compressible tube forces dental paste inside of the tube out of an opening in the second end of the tube and onto the brush.

14 Claims, 5 Drawing Sheets

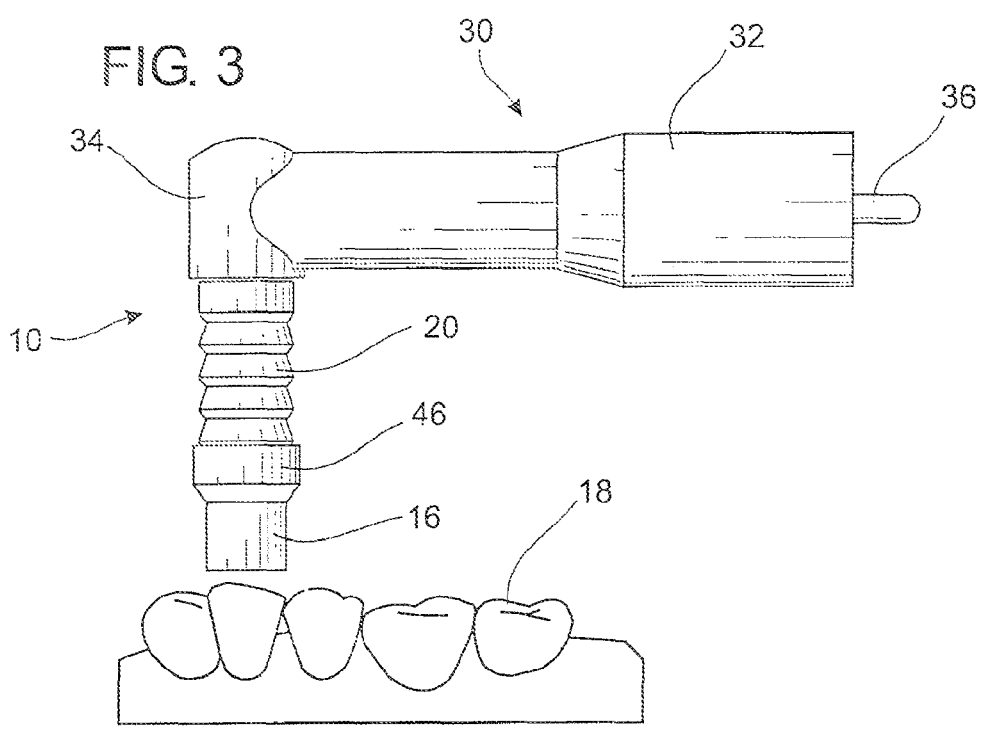
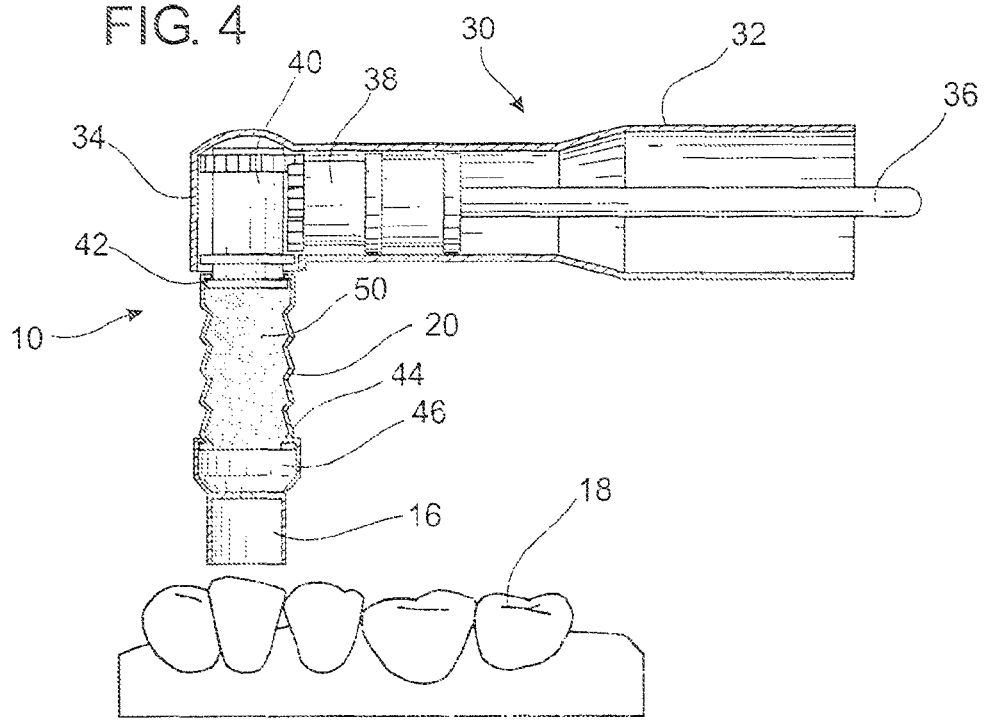

COMBINATION ROTATING DENTAL CLEANING BRUSH AND PASTE DEVICE

CROSS-REFERENCE TO PENDING APPLICATIONS

This application is a continuation-in-part patent application of U.S. patent application Ser. No. 10/906,861 filed Mar. 9, 2005, entitled "A Combination Rotating Dental Cleaning Brush and Paste Device", which is a continuation-in-part patent application of U.S. patent application Ser. No. 10/418,235 filed Apr. 17, 2003, now U.S. Pat. No. 6,875,017, which is based on U.S. Provisional Patent Application No. 60/404,563 filed Aug. 20, 2002.

BACKGROUND OF THE INVENTION

1. Field of the Invention

The present invention is directed to a combination rotating dental cleaning brush and paste device wherein paste is stored in an accordion tube whereby axial pressure on the tube forces paste onto the brush. In particular, the present invention provides a combination rotating dental cleaning brush and paste device whereby paste is delivered to the brush at a rate as desired without additional switching or manipulation and without varying from the normal operation of the device.

2. Prior Art

Various rotating dental cleaning and prophylaxis polishing tools have been utilized in the past by dentists and dental technicians for removal of plaque and stains. In a typical rotating dental cleaning tool, a cylindrical portion is provided with a shaft passing therethrough. The shaft terminates in a drive shaft gear head which meshes with a driven gear member oriented at a ninety degree (90°) angle to the axis of rotation. The rotating tool has a right angle bend and is typically held by a dentist or a dental technician. A polishing cup is set at a right angle to the rotary hand piece. The dental tool is driven by powered equipment normally found in a dental office, such as AC motor power, DC motor power, pneumatic power or hydraulic power.

The standard practice is to periodically remove the rotating brush from the patient's mouth and dip it into a paste container containing dental paste. At one time, the tools were primarily made of metal and other materials and were sanitized after each use. More recently, the tools and brushes have been fabricated from inexpensive plastic and are simply disposed of after each use.

Because the repeated removal of the brush and dipping into the paste container requires a number of steps, various proposals have been made in the past to store the dental paste in the tool or housing of the tool itself. Some of these proposals involve spring or thumb activated mechanisms which require a finger of the dentist or dental technician to advance the mechanism in order to force the paste out to the brush. While these proposals eliminate the need for a separate container of dental paste, they are somewhat unwieldy.

Other proposals for delivery of the paste to the brush move the paste onto the brush by action of the rotary shaft. For example, see Lewis et al. (U.S. Pat. No. 3,389,468) wherein a plunger 62 is carried by a drive shaft 22 so that rotation of the drive shaft forces paste into a polishing cup.

Warden et al (U.S. Pat. No. 4,266,933) discloses a spiral wiper element which continually moves paste into a polishing cup.

Roth et al (U.S. Pat. No. 5,692,901) discloses an attachment with integral feed mechanism to expel paste into a polish cup. Rotation of the drive shaft propels paste via a propellant screw.

These proposals suffer in that the paste may not be delivered at the same rate as it is desired.

There remains a need for a combination rotating dental cleaning brush and paste device which is disposable and prepackaged for use with dental paste stored therein.

There remains a need for a combination rotating dental cleaning brush and paste device wherein dental paste may be stored in the device and delivered to the brush at a rate and at such times as are desired by the dentist or the dental technician.

There also remains a need for a combination rotating dental cleaning brush and paste device whereby dental paste may be delivered to the brush by simple axial movement of a compressible tube without further manipulating the tool or taking other actions.

SUMMARY OF THE INVENTION

The present invention is directed to a combination rotating dental cleaning brush and paste device which is attached to a standard, hand-held instrument held in the hand of a dentist, a dental technician or an individual user.

The device includes a compressible tube which stores a measured dose of dental paste. The tube may be axially compressed from an original position to a compressed position. The device includes a housing having a first cylindrical portion and a second cylindrical portion oriented at a 90° angle to the first portion. The cylindrical housing has a rotating shaft passing thereto. The rotating shaft is rotated by mechanical, hydraulic, pneumatic or other means.

The shaft rotates a first gear which, in turn, rotates a second gear at a right angle thereto. The second gear is connected to a first end of the accordion tube. A second end of the tube terminates in a knob which is rotated by the second end of the accordion tube. A resilient, flexible prophy cup or brush is rotated by the second end of the accordion tube and snap fits over the knob.

In operation, the shaft is rotated which rotates the first gear. In turn, the second gear is rotated which causes rotation of the tube and the connected knob. Finally, rotation of the knob causes rotation of the brush or cup. There is an opening through the knob.

As the device is brought to bear against the tooth or teeth of a patient, the tube can be caused to be axially compressed, thereby causing dental paste to be forced out of the tube, through the opening in the knob, and into the cup or brush so that the dental paste will be applied to the teeth of the patient.

BRIEF DESCRIPTION OF THE DRAWINGS

FIG. 3 illustrates a side view of the device shown in FIG. 1 and FIG. 4 illustrates the device shown in FIG. 3 with portions partially cut away;

DESCRIPTION OF THE PREFERRED EMBODIMENTS

The embodiments discussed herein are merely illustrative of specific manners in which to make and use the invention and are not to be interpreted as limiting the scope of the instant invention.

While the invention has been described with a certain degree of particularity, it is to be noted that many modifications may be made in the details of the invention's construction and the arrangement of its components without departing from the spirit and scope of this disclosure. It is understood that the invention is not limited to the embodiments set forth herein for purposes of exemplification.

Figure 1:
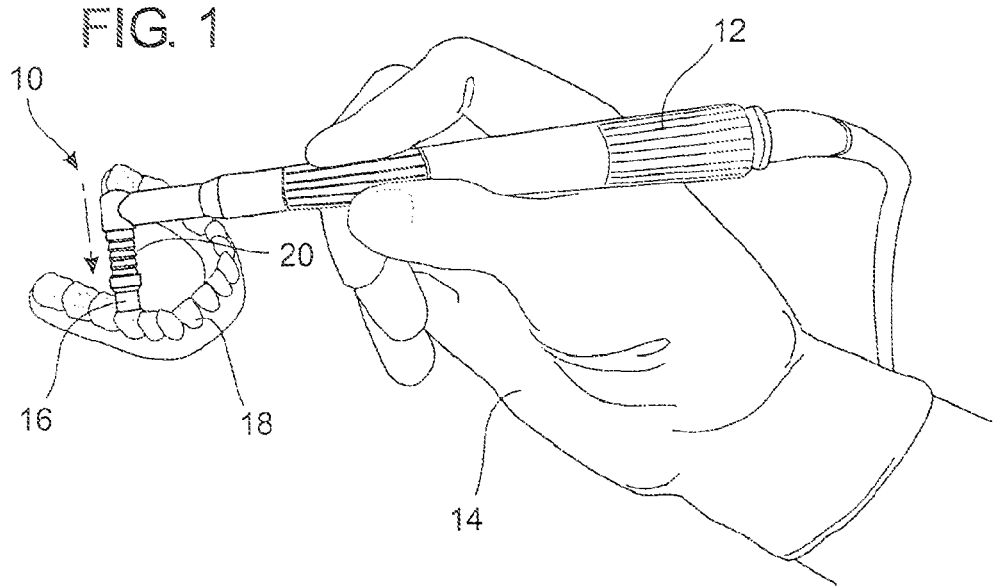
FIG. 1 illustrates a perspective view of a combination rotating dental cleaning brush and paste device constructed in accordance with the present invention.

Referring to the drawings in detail, FIG. 1 illustrates a perspective view of a combination rotating dental cleaning brush and paste device 10 constructed in accordance with the present invention. The device 10 is attached to a standard hand-held instrument 12 which is held in the hand 14 of a dentist or dental technician. A normal grip is maintained throughout operation of the device so that extraordinary action is not required by the dentist or the dental technician.

The device 10 of the present invention operates as a prophylaxis or prophy angle attachment and attaches to a standard dental instrument. The device 10 terminates in a standard, resilient, flexible prophy cup which is brought over and onto teeth 18 of a patient.

As will be described herein, the prophy cup is rotated by a system of gears to polish and brush the teeth 18 of a patient.

Figure 2:
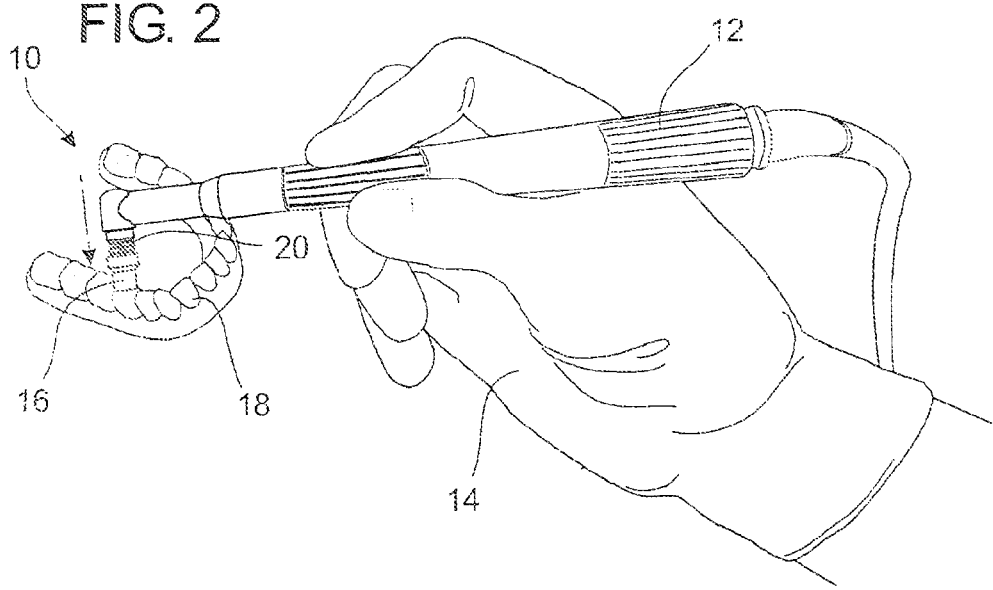
FIG. 2 illustrates a perspective view of the combination rotating dental cleaning brush and paste device as shown in FIG. 1 with an accordion tube axially compressed.

The device 10 includes an accordion tube 20 which will be described in detail. The accordion tube 20 stores a measured dose of dental paste. The accordion tube 20 may be axially compressed from the original position shown in FIG. 1 to the compressed position shown in FIG. 2.

FIG. 3 illustrates a side view of the device 10 above a set of teeth 18 apart from the standard instrument 12, while FIG. 4 illustrates a side view of the device with portions partially cut away.

The device 10 includes a housing 30 having a first cylindrical portion 32 and a second cylindrical portion 34 which is oriented at a ninety degree (90°) angle to the first portion 32.

The cylindrical housing 30 has a rotating shaft 36 passing axially therethrough. The shaft 36 will be rotated by action of the hand-held instrument.

As best seen in FIG. 4, the shaft 36 rotates a first gear 38 which, in turn, rotates a second gear 40 at a right angle or a ninety degree (90°) angle thereto.

The second gear 40 is connected to a first end 42 of the accordion tube 20. A second end 44 of the accordion tube opposed to the first end terminates in a knob 46 which is rotated by the second end 44 of the accordion tube. A cup or brush 16 is attached to and is rotated by the second end of the accordion tube.

Dental paste 50 is preloaded and stored within the confines of the accordion tube as seen in FIG. 4. Various types of dental paste might be used within the scope of the present invention.

Figure 5:
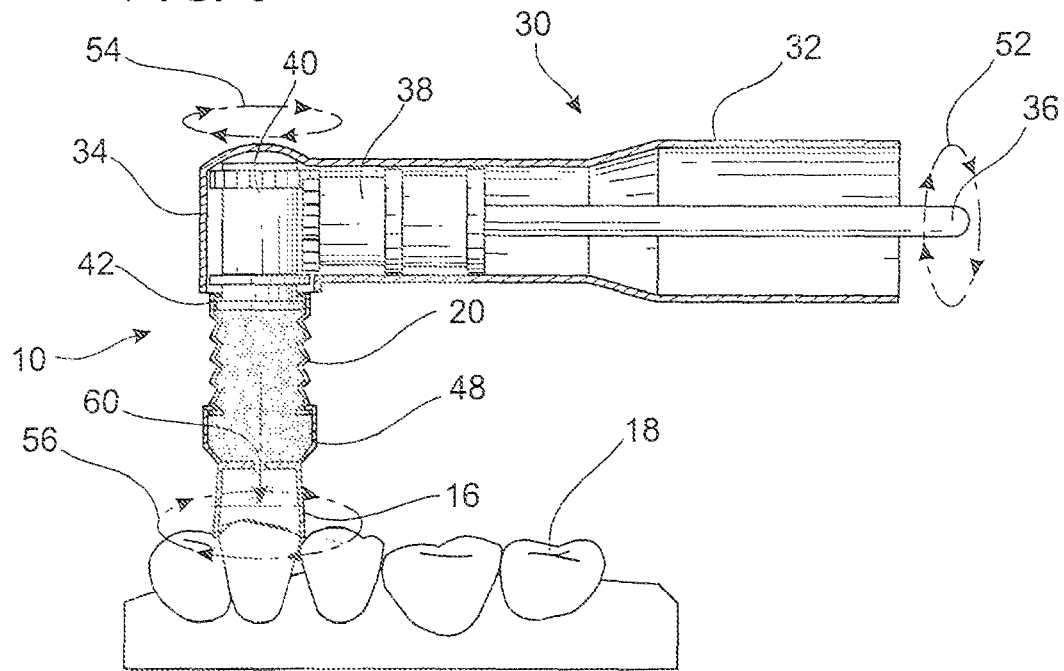
FIGS. 5 and 6 illustrate the combination disposable rotating dental cleaning brush and dental paste of the present invention in partial sectional view illustrating in sequence the delivery of the dental paste.
Figure 6:
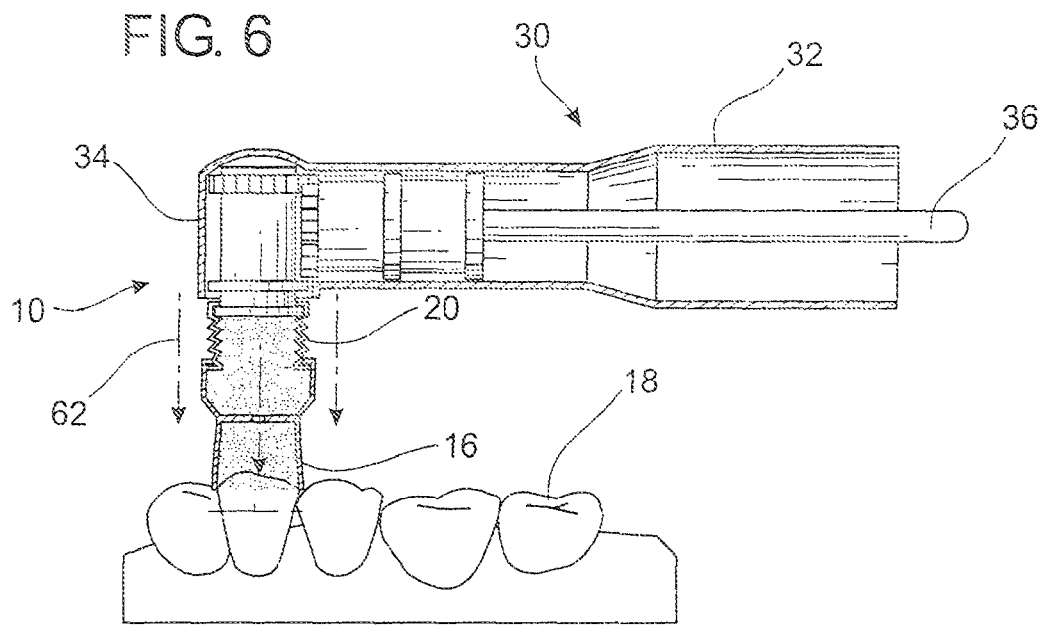

FIGS. 5 and 6 illustrate the sequential operation of the device 10. As the shaft 36 is rotated as illustrated by arrows 52, the first gear 38 is rotated and, in turn, the second gear 40 is rotated as illustrated by arrows 54.

This force causes rotation of the accordion tube 20 and the knob 48. Finally, rotation of the knob 48 causes rotation of the brush or cup 16 as illustrated by arrows 56.

As seen in FIGS. 5 and 6, there is an opening 60 in the knob. As the device 10 is brought to bear against the tooth or teeth 18 of the patient, the accordion tube 20 will be caused to be axially compressed, causing dental paste to be forced out of the accordion tube 20, through the opening 60 in the knob, and into the interior of the cup or brush 16 so that the dental paste will be applied to the teeth of the patient.

As seen in FIG. 5, paste is beginning to move through opening 60 in the knob.

FIG. 6 shows the axial compression of the accordion tube 20 and the movement of the paste from the accordion tube out through the opening 60 and on to the brush and teeth of the patient. Arrows 62 illustrate the axial compression movement of the tube.

The device 10 may be prepackaged with a measured dose of dental paste which will be adequate to clean a patient's teeth. Once the cleaning operation has been completed, the device may be discarded.

Figure 7:
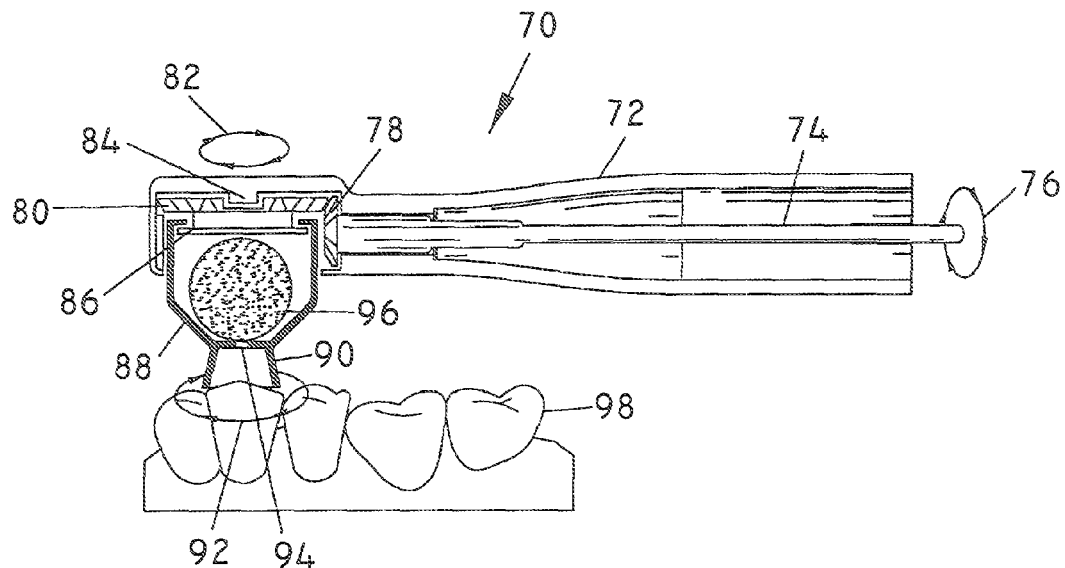
FIGS. 7 and 8 illustrate an alternate embodiment of the combination disposable rotating dental cleaning brush and dental paste illustrating in sequence the delivery of the dental paste.
Figure 8:
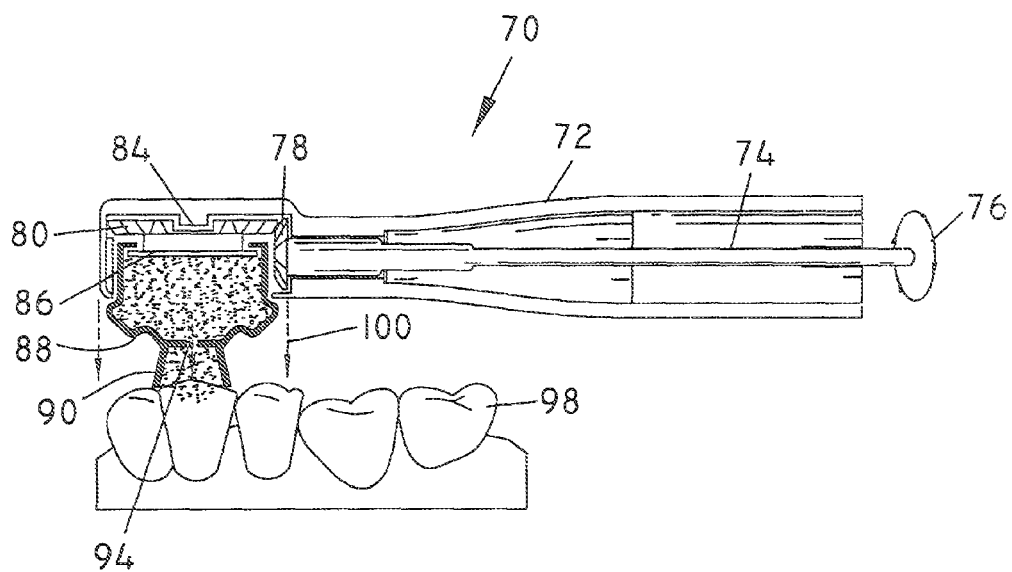

FIGS. 7 and 8 illustrate sequential operation of a second, preferred embodiment 70 of the device. The device 70 includes a housing 72 having a first cylindrical portion and a second cylindrical portion which is oriented at a ninety degree (90°) angle to the first portion.

The cylindrical portion has a rotating shaft 74 passing axially therethrough. The shaft 74 will be rotated by action of the hand-held instrument as previously described in detail. The shaft 74 is rotated as illustrated by arrows 76. As the shaft is rotated by arrows 76, a first gear 78 extending from the shaft is rotated. Rotation of the first gear 78 causes rotation of a second gear 80 which is engaged with the first gear. The second gear 80 is rotated as illustrated by arrows 82 in FIG. 7. The second gear 80 includes an axially extending post 84 which is received in a recess in the housing 72. The second gear 80 also includes a radially extending disk 86 which rotates along with the second gear 80. The rotational force of the second gear 80 and the disk 86 causes rotation of a compressible tube 88.

The compressible tube 88 has a first end which is rotated by the extending disk 86 and is held in place by a shoulder and lip of the compressible tube 88. Extending from an opposed, second end of the compressible tube 88 is a brush 90 which is integral with, connected to, and rotated by the compressible tube 88. The brush 90 is rotated as illustrated by arrows 92.

As seen in FIGS. 7 and 8, there is an opening 94 through the second end of the compressible tube 88. Dental paste may be stored within the compressible tube. In one embodiment, dental paste may be stored in a bead 96 which will release dental paste upon compression or upon piercing. As the device 70 is brought to bear against a tooth or teeth 98, the compressible tube 88 will be caused to be axially compressed, causing dental paste to be forced out of the bead 96 and forced out of the opening 94 and into the interior of the cup or brush 90 so that dental paste will be applied to the teeth 98 of the patient.

FIG. 8 shows the axial compression of the compressible tube 88 and the movement of the dental paste from the compressible tube out through the opening 94 and onto the brush 90 and the teeth 98 of the patient. Arrows 100 illustrate the axial compression movement of the tube.

The device 70 may be prepackaged with a measured dose of dental paste adequate to clean a patient's or user's teeth. Alternatively, a bead 96 containing a measured dose of dental paste may be prepackaged within the compressible tube or may be inserted into the tube. Once the cleaning operation has been completed, the device 70 may be discarded.

Figure 9:
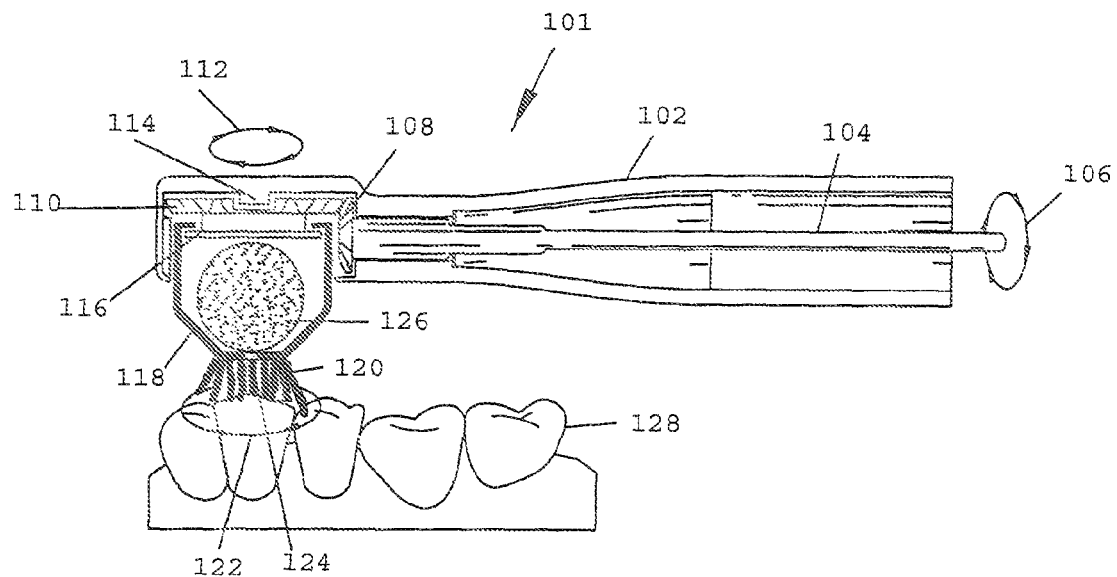
FIGS. 9 and 10 illustrate a further alternate embodiment of the combination disposable rotating dental cleaning brush and dental paste illustrating in sequence the delivery of the dental paste.
Figure 10:
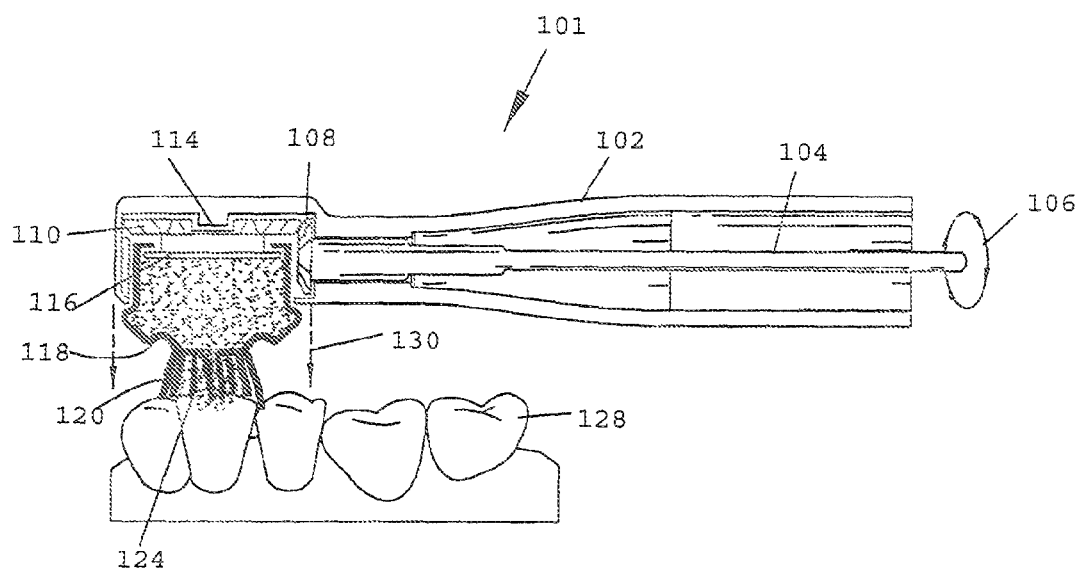

FIGS. 9 and 10 illustrate sequential operation of yet a third, preferred embodiment 101 of the device. The device 101 includes a housing 102 with a rotating shaft 104 passing axially therethrough. The device may be connected to and driven by a wide variety of electric toothbrushes (not shown).

In one preferred embodiment, the housing 102 includes a first cylindrical portion and a second cylindrical portion oriented at a ninety degree (90°) angle to the first cylindrical portion.

The cylindrical portion has a rotating shaft 104 which will be rotated by action of a toothbrush or hand-held instrument. The shaft 104 is rotated as illustrated by arrows 106. The shaft 104 terminates in a rotating connector 116.

In one preferred embodiment, as the shaft is rotated, a first gear 108 extending from the shaft is rotated. Rotation of the first gear 108 causes rotation of the second gear 110 which is engaged with the first gear 108. The second gear 110 is rotated as illustrated by arrows 112 in FIG. 9. The second gear 110 includes an axially extending post 114 which is received in the recess in the housing 102. The axially extending post 114 also includes a radially extending disk 116 which rotates along with the second gear 110. The rotational force of the shaft 106 causes rotation of a compressible tube 118. The compressible tube 118 has a first end rotated by the shaft and is held in place by a shoulder and lip of the compressible tube 118. Extending from an opposed, second end of the compressible tube 118 is a brush 120 having a plurality of bristles. The brush 120 is integral with, connected to and rotated by the compressible tube 118. The brush 120 is rotated as illustrated by the arrows 122.

As seen in FIGS. 9 and 10, there is an opening 124 through the second end of the compressible tube 118. Dental paste may be stored within the compressible tube. The dental paste may be stored in many forms. As the device 101 is brought to bear against a tooth or teeth 128, the compressible tube 118 will be caused to be axially compressed, causing dental paste to be forced out of the opening 124 and into the interior of the brush 120 so that dental paste will be applied to the teeth 128 of the user.

FIG. 9 shows the axial compression of the compressible tube 118 and the movement of the dental paste from the compressible tube out through the opening 124 and onto the brush 120 and the teeth of the user. Arrows 130 illustrate the axial compression movement of the compressible tube. The device 101 can be pre-packaged with a measured dose of dental paste adequate to clean a user's teeth. Once the cleaning operation has been completed, the device 101 may be discarded.

Whereas, the present invention has been described in relation to the drawings attached hereto, it should be understood that other and further modifications, apart from those shown or suggested herein, may be made within the spirit and scope of this invention.

What is claimed is:

1. A combination rotating dental cleaning brush and paste device, said device comprises:

a housing having a rotating shaft therethrough;
   a compressible tube having two opposed ends, a first end which is connected to and rotatable by said shaft and an opposed second end;
   a brush connected to and rotatable by said second end; and
   dental paste inside said compressible tube whereby axial compression of said tube by pressing said brush against the teeth of a patient forces said paste out of said second end.

2. The combination brush and paste device as set forth in claim 1 wherein said brush includes a plurality of bristles.

3. The combination brush and paste device as set forth in claim 1 wherein said housing has a first cylindrical portion and a second portion in angular relation therewith.

4. The combination brush and paste device as set forth in claim 3 wherein said first cylindrical portion is oriented at a ninety degree (90°) angle to said second portion.

5. The combination brush and paste device as set forth in claim 1 wherein said rotating shaft terminates in a rotating connector.

6. The combination brush and paste device as set forth in claim 5 wherein said rotating connector is a disk.

7. The combination rotating dental cleaning brush and paste device as set forth in claim 1 wherein said second end has an opening therethrough to permit said paste to pass from said tube to said brush.

8. The combination brush and paste device as set forth in claim 5 wherein said compressible tube is removably attached to said rotating connector.

9. A method of using a combination dental cleaning brush and paste device, wherein the combination device comprises a compressible tube and a rotating shaft, said method comprises:

storing a quantity of dental paste in the compressible tube having two opposed ends, a first end connected to the rotating shaft and an opposed second end;
   rotating a brush that is integral with and connected to said compressible tube; and
   axially compressing said compressible tube to force said paste out of an opening in said second end of said tube and onto said brush, wherein said compressible tube compressed by pressing said brush against the teeth of a patient.

10. The method as set forth in claim 9 wherein said brush includes a plurality of bristles.

11. The method as set forth in claim 9 wherein said rotating shaft passes through a cylindrical housing.

12. The method as set forth in claim 9 wherein said rotating shaft terminates in a rotating connector.

13. The method as set forth in claim 12 wherein said rotating connector is a disk.

14. The method as set forth in claim 12 including the additional steps of removing said compressible tube from said rotating connector after use and replacing said compressible tube with a replacement compressible tube.

* * * * *